(12) United States Patent
Cheung et al.

(10) Patent No.: US 9,012,687 B2
(45) Date of Patent: Apr. 21, 2015

(54) PROCESS FOR ISOLATING KUKOAMINE (71) Applicant: City University of Hong Kong, Hong Kong (CN)

(72) Inventors: Hon-Yeung Cheung, Hong Kong (CN); Yuan-Yuan Li, Hong Kong (CN); Rui Di, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 0 days.

(21) Appl. No.: 14/260,870

(22) Filed: Apr. 24, 2014

(65) Prior Publication Data
US 2015/0065752 A1 Mar. 5, 2015

(30) Foreign Application Priority Data

Sep. 3, 2013 (CN) .......................... 2013 1 0394928

(51) Int. Cl.
*C07C 233/05* (2006.01)
*C07C 231/24* (2006.01)
(52) U.S. Cl.
CPC .................................. *C07C 231/24* (2013.01)

(58) Field of Classification Search
USPC ........................................ 564/153, 157, 158
See application file for complete search history.

(56) References Cited

FOREIGN PATENT DOCUMENTS

WO    WO 2012/062026    *    5/2012

OTHER PUBLICATIONS

Piletska et al, J. of Agricultural & Foof Chemistry, 2012, 60(1), 95-99.*
Funayama et al, Phytochemistry, 1995, 38(6), 1529-31.*
Page et al, Bioorganic & Medicinal Chem. Letters, 1998, 8(13), 1751-56.*

* cited by examiner

*Primary Examiner* — Shailendra Kumar
(74) *Attorney, Agent, or Firm* — McDonnell Boehnen Hulbert & Berghoff LLP (57) ABSTRACT

The present invention provides a process for isolating kukoamine by solid phase extraction using a polyamide or a derivative thereof as an adsorbent. Said process is convenient, economical and environmental-friendly, and obtains highly purified kukoamines with a high yield.

14 Claims, 7 Drawing Sheets

PROCESS FOR ISOLATING KUKOAMINE

CROSS REFERENCE TO RELATED APPLICATIONS

The present application claims priority under 35 U.S.C. §119 to Chinese Patent Application No. 201310394928.8, filed on Sep. 3, 2013, the entire contents of which are incorporated herein by reference.

FIELD OF THE INVENTION

The present invention belongs to the field of isolation and purification. Specifically, the present invention relates to a process for isolating kukoamine.

BACKGROUND OF THE INVENTION

Kukoamine, including kukoamine A, kukoamine B and other derivatives, is one kind of spermine alkaloids. It has been regarded as a potential drug and a significant component in functional foods due to its various bioactivities, such as anti-inflammatory, anti-oxidative and hypotensive effects.

For example, WO 2012/062026 disclosed the preparation of salts of kukoamine B and their use in the treatment of sepsis and autoimmune disease.

Compared to chemical synthesis, it is much more effective, economical and environmental-friendly to isolate kukoamine from plants or other biological sources. However, such isolation and/or purification is very challenging technically because kukoamine is water-soluble and readily oxidized.

Elena V. Piletska et al. (Agricultural and Food Chemistry, 2012, 60, p. 95-99) disclosed a process for isolating kukoamine A from potato skins by solid phase extraction using a molecularly imprinted polymer. However, said process required designing on computer, screening and synthesizing the molecularly imprinted polymer.

Other isolating processes in the prior art are highly relied on repeated column chromatography, which is low efficient and time consuming. Further, organic solvents in a large volume are required, resulting in very poor yield as the greatest disadvantage. In addition, the final product has a low purity due to self-oxidation during the isolation.

Therefore, a convenient isolating process for obtaining highly purified kukoamine with a high yield is desired.

The above information disclosed in the background portion is only for purpose of enhancing understanding of the background of the present disclosure, and thus it may include information which does not constitute prior art known to one of ordinary skill in this art.

SUMMARY OF THE INVENTION

The present disclosure provides a rapid, economical and environmental-friendly process for isolating kukoamine from samples, such as plants or other biological sources.

Accordingly, in one aspect, the present disclosure provides a process for isolating kukoamine, comprising contacting a polyamide or a derivative thereof as an immobile phase with a solution of a crude extract of kukoamine, so as to adsorb the kukoamine.

The kukoamine used therein may be, for example, any one of compounds having the following structures or a mixture thereof:

Kukoamine derivative 2

Kukoamine derivative 3

Kukoamine derivative 4

Kukoamine derivative 5

Kukoamine derivative 6

Kukoamine derivative 7

In some embodiments, the polyamide may be a polymer having amide group(s), such as, but not limited to, polyamide 6 (nylon 6), polyamide 66 (nylon 66), polyamide 1010 (nylon 1010), polyaramide and the like. Derivatives of the polyamide are modified polyamides with a polyamide as the parent nucleus.

A person skilled in this art would be able to select a polyamide or a derivative thereof having any suitable particle size for isolating kukoamine. For example, the polyamide or a derivative thereof may have a particle size of about 75 to 150 µm, such as, about 75 µm, about 90 µm, about 105 µm, about 120 µm, about 135 µm or about 150 µm.

The process of the present invention is essentially a solid phase extraction process. It is performed in such a way that kukoamine from samples is selectively adsorbed by the polyamide or a derivative thereof as an adsorbent and selectively eluted so as to achieve the isolation from the samples.

The process of the present invention may be performed, for example, in a way of solid phase column extraction, solid phase dispersive extraction, filter film (cartridge) extraction or solid phase micro-extraction.

A person skilled in this art would be able to select any suitable amount of polyamide or a derivative thereof as desired for isolating kukoamine, so as to adsorb kukoamine as completely as possible. For example, polyamide or a derivative thereof may be used in an amount at a ratio of kukoamine to be isolated to the polyamide or a derivative thereof, such as, 1 mg of kukoamine to about 0.02 to 1 g of polyamide, e.g., 1 mg of kukoamine to about 0.05 to 0.2 g of polyamide, such as, 1 mg of kukoamine to about 0.1 g, 0.12 g or 0.16 g of polyamide.

In some embodiments of the present invention, in the process for isolating kukoamine, contacting may be repeated for more than one times.

In some embodiments of the present invention, the process further comprises eluting the kukoamine adsorbed on the polyamide or a derivative thereof as an immobile phase using an acidic solution after contacting.

In some embodiments of the present invention, the acidic solution for elution may have a pH of less than 5 and be an aqueous or alcoholic solution of acetic acid or a salt thereof, formic acid, hydrochloric acid, phosphoric acid or a salt thereof, trifluoroacetic acid or the like. The alcoholic solution may be, but not limited to a solution in a lower alcohol having a carbon number of less than 6 and being miscible with an aqueous solution. In some embodiments of the present invention, the alcoholic solution may be a solution in methanol, ethanol, propanol or iso-propanol. In some embodiments of the present invention, the acidic solution is an aqueous acetic acid solution having a concentration between about 0.1 vol % and 5 vol %, or other acidic solutions having a corresponding pH value. In some embodiments of the present invention, the acidic solution for elution may be an aqueous acetic acid solution having a concentration of about 0.5 vol %.

In some embodiments of the present invention, the crude extract of kukoamine may be an extract obtained from, but not limited to Lycii Cortex, potato skin, tomato, eggplant or cultures of tissue cells having similar ingredients. It may also be commercially available.

The crude extract may be obtained according to any conventional method known in this art. The conventional method may include, but not limit to, the following key steps: 1) sonicated extraction, or hot reflux extraction, or extraction under room temperature, or microwave-assisted extraction, etc.; 2) filteration; 3) drying with spray dryer or vacuum dryer or freeze dryer or rotary evaporator, etc.

In some embodiments of the present invention, the process may further comprise dispersing the crude extract of kukoamine in a polar solvent so as to obtain a solution of the crude extract of kukoamine by filtering before contacting. In some embodiments of the present invention, the polar solvent for the dispersing may be water, or an aqueous alcohol, acetonitrile or acetone solution having a concentration, such as about 10 vol % to 50 vol %. In some embodiments of the present invention, the alcohol may be a lower alcohol having a carbon number of less than 6 and be miscible with an aqueous solution, such as methanol, ethanol propanol or iso-propanol. In some embodiments of the present invention, the polar solvent is an aqueous methanol or ethanol solution having a concentration of about 10 vol % to 50 vol %, such as, an aqueous ethanol solution having a concentration of about 50 vol %.

In some embodiments of the present invention, the process may further comprise washing with water and an aqueous alcohol solution after contacting and before eluting. In some embodiments of the present invention, the aqueous alcohol solution may be an aqueous solution of a lower alcohol having a carbon number of less than 6, such as, an aqueous solution of methanol, ethanol propanol or iso-propanol, e.g., an aqueous solution of methanol or ethanol having a concentration of about 50 vol %.

In some embodiments of the present invention, the process further comprise separating the polyamide or a derivative thereof having kukoamine adsorbed thereto after contacting and before washing. In some embodiments of the present invention, the separation may be carried out by means of, such as filtration.

In some embodiments of the present invention, the process may further comprise purifying the isolated kukoamine after eluting.

In some embodiments of the present invention, the kukoamine obtained by the solid extraction may be further purified by preparative or semi-preparative liquid chromatography. For example, such purification may be performed by low pressure, middle pressure or high pressure preparative liquid chromatography.

Figure 1:
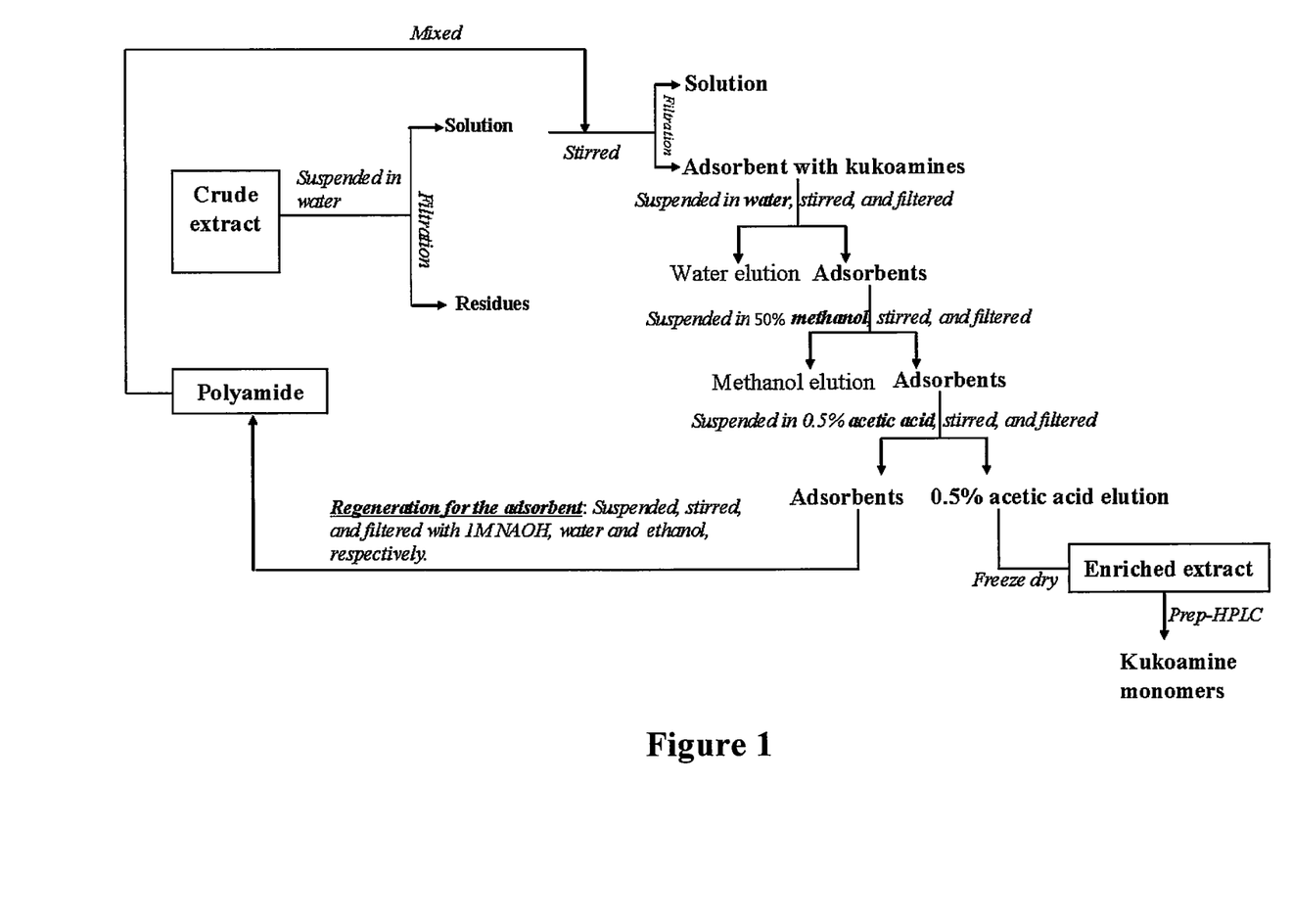
FIG. 1 is a schematic flow chart showing one embodiment of the process for isolating kukoamine.

In a detailed embodiment of the present invention (referring to FIG. 1), the process for isolating kukoamine of the present invention comprises the following steps:

a dispersing step, wherein, for example, a crude extract of kukoamine is dispersed in a polar solution such as water, to obtain a solution of the crude extract of kukoamine (i.e. an extract solution), such as, an aqueous solution of the crude extract of kukoamine, by filtering;

a contacting step, wherein, for example, polyamide (such as nylon 6, nylon 66, nylon 1010 or polyaramide) or a derivative thereof is mixed with the solution of the crude extract of kukoamine obtained in the previous step;

a separating step, wherein, for example, a mixture obtained in the previous step is filtered to give polyamide or a derivative thereof having kukoamine adsorbed thereto;

a washing step, wherein, for example, the polyamide or derivatives thereof having kukoamine adsorbed thereto from the previous step is dispersed in water, and stirred. Thereafter, it is filtered to give the polyamide or a derivative thereof having kukoamine adsorbed thereto. The obtained polyamide or a derivative thereof having kukoamine adsorbed thereto is then dispersed in methanol, such as an aqueous methanol solution have a concentration of 50 vol %, and stirred. Thereafter, it is filtered to give the polyamide or a derivative thereof having kukoamine adsorbed thereto;

an eluting step, wherein, for example, kukoamine is eluted from the polyamide or a derivative thereof having kukoamine adsorbed from the previous step with an acidic solution, such as, an aqueous or alcoholic solution of acetic acid or a salt thereof, formic acid, hydrochloric acid, phosphoric acid or a salt thereof or trifluoroacetic acid having a pH of less than 5, e.g., an aqueous acetic acid solution having a concentration of about 0.5 vol %.

Thereafter, the obtained eluate is freeze-dried to give enriched kukoamine.

Optionally, the enriched kukoamine obtained in the previous step may be further purified by means of preparative or semi-preparative liquid chromatography to give kukoamine monomers.

In the present invention, the polyamide or a derivative thereof may be reused after being regenerated, such as, by using NaOH, methanol, ethanol or the like.

The present process for isolating kukoamine is based on hydrogen bond interaction between kukoamine and the polyamide or a derivative thereof. Such an interaction may be reversed by an acidic solution. By applying the process of the present invention, the purity of kukoamine, based on total amount of kukoamines A and B, may be enhanced to 60 wt % from about 1.5 wt % in the initial form. The purity has been increased about 40 times. Kukoamine monomers having a purity greater than 95% may be achieved by means of preparative liquid chromatography.

In other aspect, the present invention provides use of a polyamide or a derivative thereof in the isolation of kukoamine.

In some embodiments of the present invention, the polyamide may be, but not limited to, nylon 6, nylon 66, nylon 1010 or a polyaramide.

The process of the present invention has the following advantages.

One-step procedure for targeted adsorption: in the present invention, kukoamine can be specifically transferred to the polyamide or a derivative thereof from the solution so as to avoid a loss of kukoamine caused by repeated dissolution in multiple steps.

Easily available adsorbent: commercially available polyamide or a derivative thereof may be used without a special synthesis.

Environmentally friendly: in the present process, consumption of organic solvents as in the case of conventional column chromatography can be significantly reduced, because repeated elution, concentration and re-dissolution necessary in the conventional column chromatography are avoided.

Easy regeneration of adsorbent: the polyamide or a derivative thereof may be easily regenerated using NaOH, methanol or ethanol. The regenerated adsorbent is not influenced in its adsorbing performance.

Therefore, the present invention provides a process for specifically isolating and purifying kukoamine from samples, such as biomaterials, which is rapid, economical, environmentally friendly and easily operated.

The use of the word "a" or "an" used in the claims and/or the specification may mean "one", but it is also consistent with the meaning of "one or more", "at least one", and "one or more than one".

DETAILED DESCRIPTION OF THE INVENTION

Example 1

Isolation of Kukoamine by Extraction Using Polyamide

Figure 2:
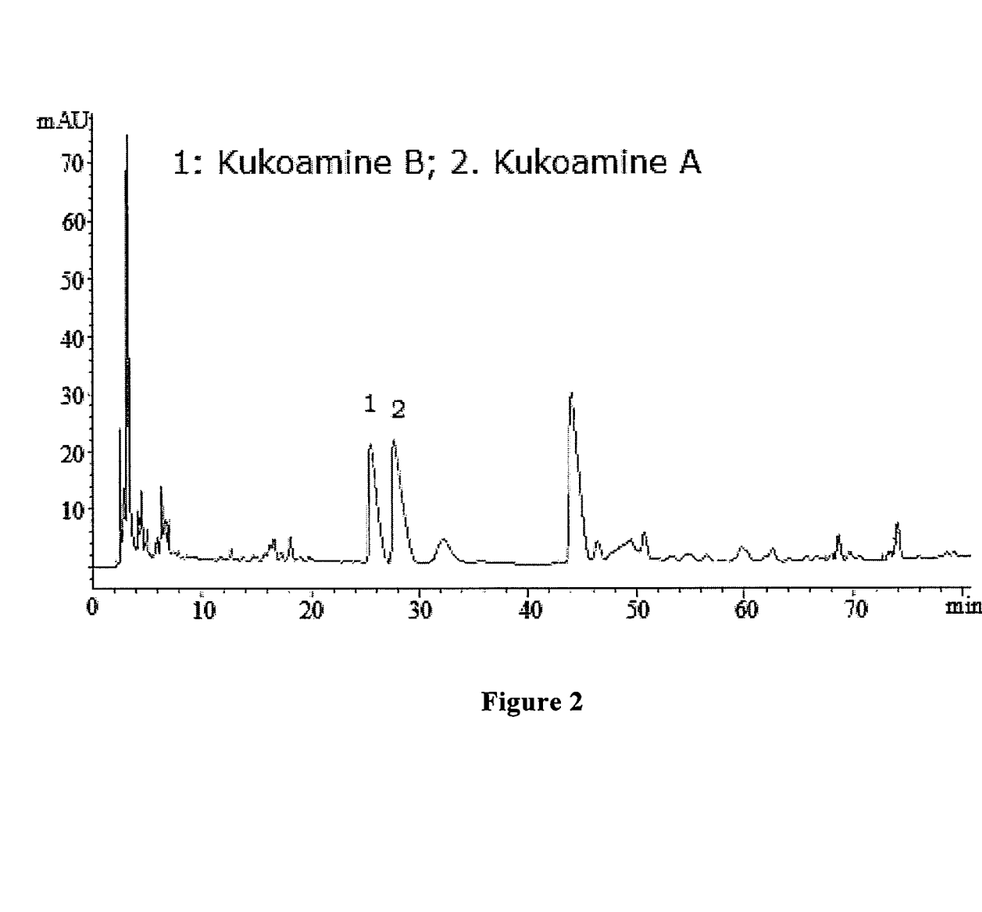
FIG. 2 shows the chromatograph of a crude extract of kukoamine obtained from Lycii Cortex.

Lycii Cortex (5 kg) was added to 50 vol % aqueous ethanol solution 10 times in volume in an ultrasonic extraction device (Beijing Hongxianglong Bio. Tech. Ltd.), and was extracted 2 times at 50 Hz for 1 hour per time. The extract was transferred to a spray drier (BUCHI, Switzerland), and was dried instantly at 80° C. to give about 500 g of a crude extract as powder containing kukoamine. 10 mg of the crude extract was dissolved in 1 mL of water. After complete dissolution, it was filtered by a microporous filter membrane of 0.22 micrometer, and then was injected into a HPLC instrument for measurement. HPLC: Agilent, U.S.; column. Agilent Zorbax C18 SB-AQ (250 mm×4.6 mm i.d., 5 μm); mobile phase: 0.1 vol % aqueous trifluoroacetic acid solution (A) and methanol (B) were used in linear gradient elution from 8.5 vol % B to 12 vol % B, running for 35 min; flow rate: 1.00 mL/min; column temperature: 40° C.; injection volume: 10 μL; detection wavelength: 230 nm. Therefrom the chromatograph of the crude extract was obtained (see FIG. 2). The content of kukoamine (based on total amount of kukoamine A and kukoamine B) was quantitatively determined to be about 1.5 wt % according to an external standard method, specifically the contents of kukoamine A and kukoamine B were about 0.14 wt % and 1.4 wt %, respectively.

Figure 3:
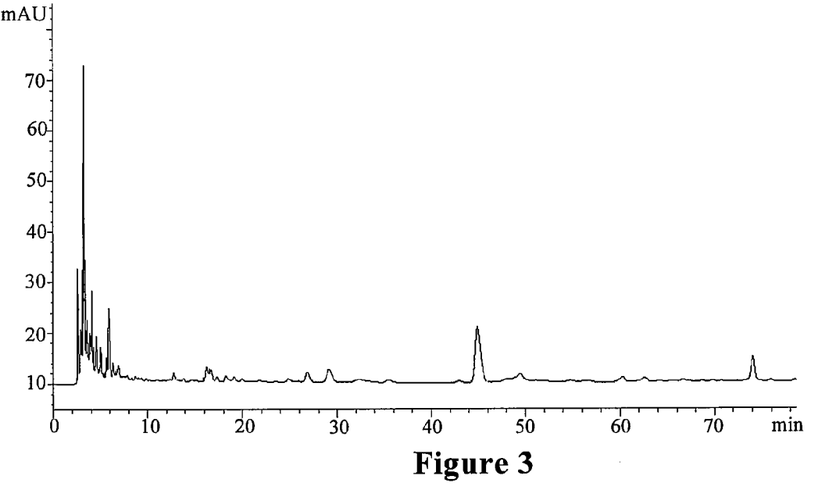
FIG. 3 shows the chromatograph of filtrate after solid phase extract by polyamide.
Figure 4:
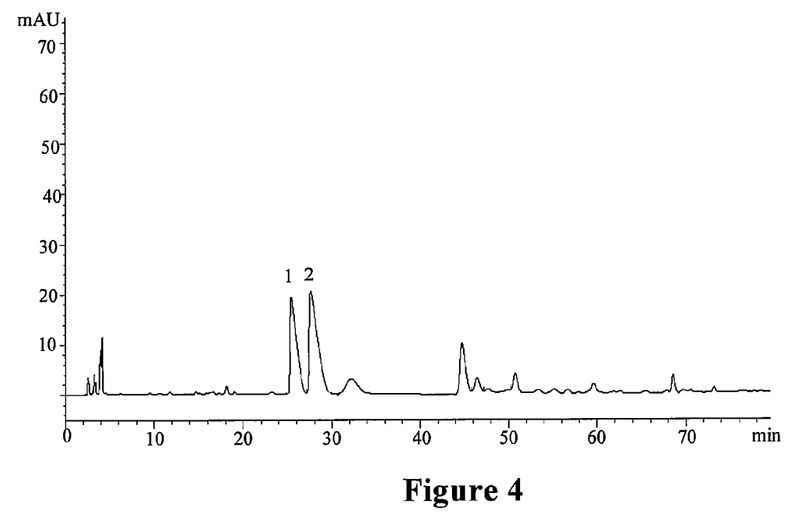
FIG. 4 shows the chromatograph of the eluate obtained by eluting using 0.5 vol % aqueous acetic acid solution.

27 g of the crude extract was mixed with 1000 mL of water to give an aqueous solution of the crude extract of kukoamine having a concentration of about 400 μg/mL. 25 g of polyamide (nylon 6 having a particle size of 75 μm), as immobile phase, was added into the aqueous solution of the crude extract of kukoamine. After mixing for 2 hours at the room temperature using a magnetic stirrer, the resultant mixture was filtered with suction to give the polyamide having kukoamine adsorbed. The filtrate was repeatedly contacted with polyamide (nylon 6 having a particle size of 75 μm) for 2 to 3 times using 10 g of polyamide per time. Thereafter, 1 mL of the filtrate was filtered by a microporous filter membrane of 0.22 micrometer, and then was injected into HPLC instrument and analyzed under the above mentioned conditions, to give a chromatography (FIG. 3). The amounts of kukoamines A and B in the filtrate were significantly reduced, indicating that most of the kukoamines had been adsorbed onto the polyamide from the solution. Thereafter, polyamides obtained each time were combined, suspended in 250 mL of water and 250 mL of an aqueous methanol solution having a concentration of 50 vol % successively, and rinsed in order to remove impurities. Then, the polyamides were suspended in 100 mL of 0.5 vol % aqueous acetic acid solution, and were stirred continually in order to desorb or elute the kukoamine. The solution obtained after desorption or elution, i.e. the eluate, was filtered by a microporous filter membrane, and then was injected into HPLC instrument and analyzed under the above mentioned conditions, to give a chromatography (FIG. 4). Finally, the obtained eluate was freeze-dried to give about 583 mg of enriched extract of kukoamine.

10 mg of the enriched extract of kukoamine was dissolved in 1 mL of 0.5 vol % aqueous acetic acid solution, and was measured by HPLC as described above and quantified according to the external standard method. The content of kukoamine (based on the total amount of kukoamine A and kukoamine B) in the extract was about 60 wt %.

In the isolation, enrichment rate and yield of the kukoamine were calculated according to the following formula:

Enrichment rate=content of kukoamine after isolation/purification (wt %)/content of kukoamine in the crude extract(wt %)

Yield (%)=(content of kukoamine after isolation/purification(wt %)×amount of obtained enriched extract(mg))/(content of kukoamine in the crude extract(wt %)×amount of the crude extract for isolation/purification)

The enrichment rate after such an isolation of stationery phase was 40 according to the above formula, that is, the content of kukoamine was as much as 40 times of the crude extract after isolation. The yield was 87%.

Example 2

Further Purification of Kukoamine Using Preparative Liquid Chromatography

Figure 5A:
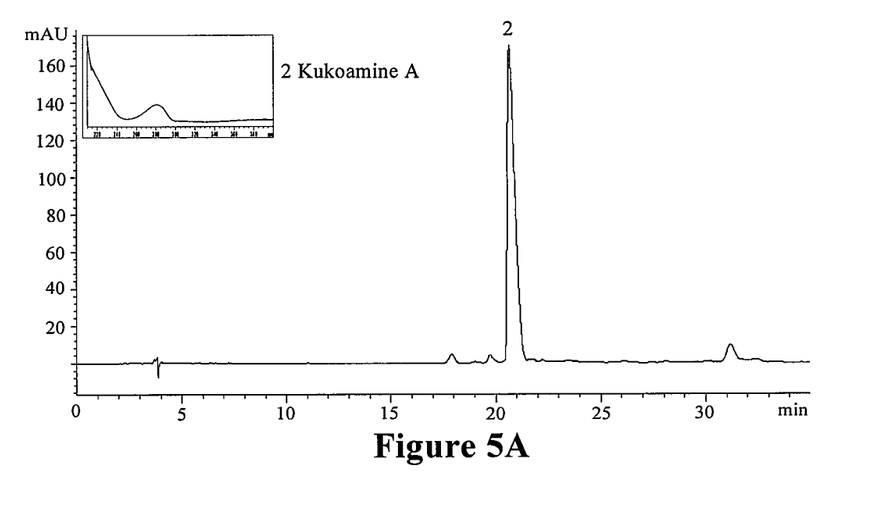
FIG. 5A and FIG. 5B show the chromatograph of kukoamine A (FIG. 5A) and kukoamine B (FIG. 5B) after further purification by means of preparative liquid chromatography.
Figure 5B:
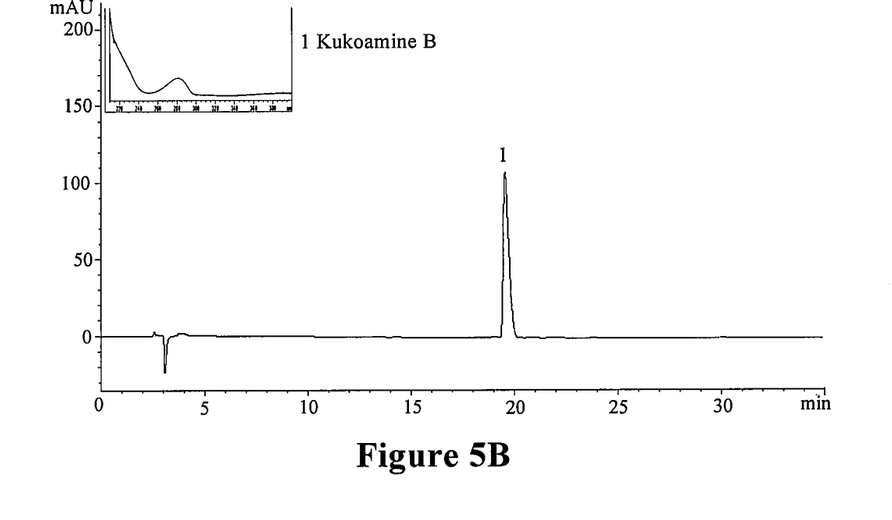
Figure 6A:
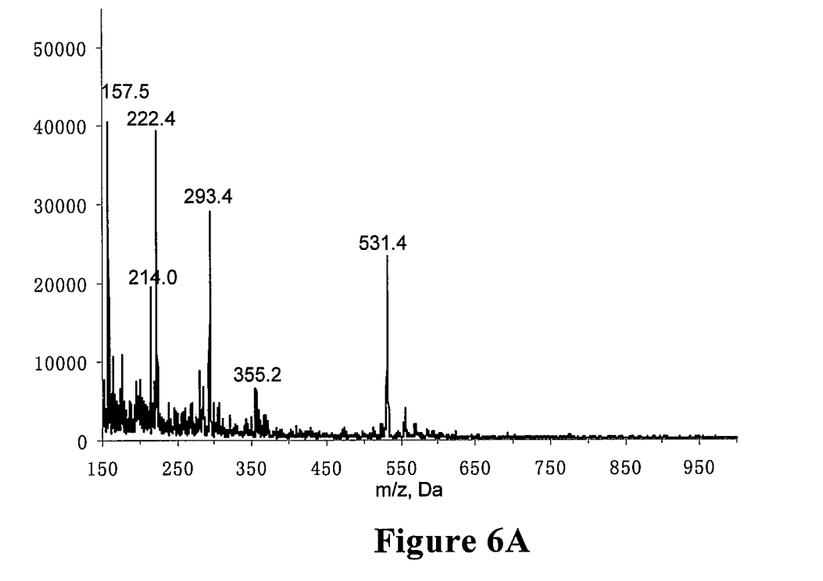
FIG. 6A and FIG. 6B show the mass spectra of kukoamine A (FIG. 6A) and kukoamine B (FIG. 6B) after further purification by means of preparative liquid chromatography.
Figure 6B:
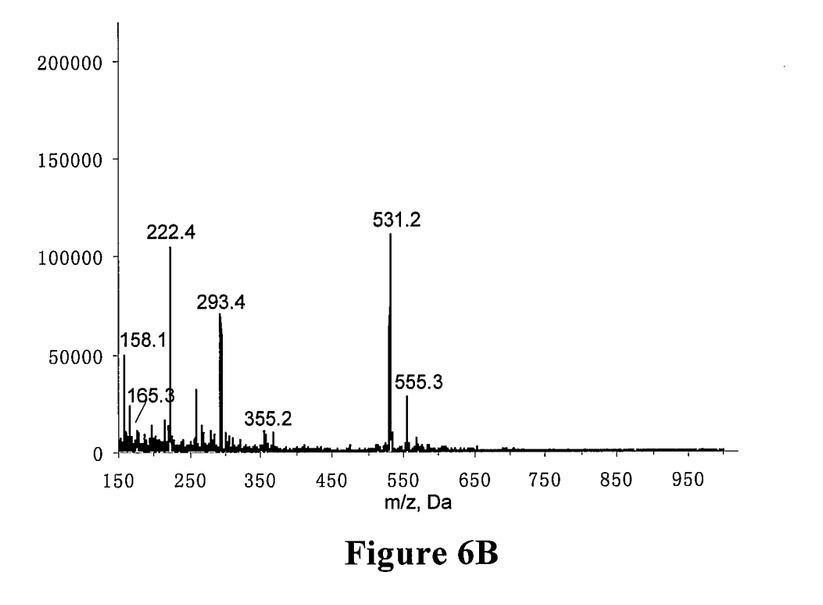

Further, the enriched extract of kukoamine obtained in Example 1 was purified by preparative liquid chromatography to give monomers of kukoamines A and B. Column: YMC pack OSD-A semi-preparative HPLC column (10 mm×250 mm, 5 μm); Instruments: Water 515 pump for both preparation and analysis, Waters 486 UV detector; isolating flow rate: 4.0 mL/min; detection wavelength: 280 nM; mobile phase: aqueous phase (phase A) was 0.1 vol % aqueous TFA solution, and organic phase (phase B) was acetonitrile; eluting program: 0 to 50 min, A: B=90:10, eluted with a constant gradient, the column was rinsed with A:B=5:95 per 5 times of isolation; collection of fractions: fractions were collected according to signals of kukoamines A and B. The collected fractions were freeze-dried, and give monomeric compounds of kukoamines A (28 mg) and B (310 mg), respectively. Monomers of kukoamines A and B were weighed for 1 mg, respectively, and were added to a 0.5 vol % aqueous acetic acid solution. After complete dissolution, the solutions were injected into HPLC instrument for analysis (at the same HPLC conditions as in Example 1), to give chromatographs of FIGS. 5A and 5B, respectively. Purity of the monomeric compounds was determined according to an area normalization method. Consequently, the kukoamine B had a purity of 98%, and the kukoamine A had a purity of 95%. Mass spectra of kukoamines A and B were shown in FIGS. 6A and 6B, respectively.

Example 3

Isolation of Kukoamine by Solid Phase Column Extraction 25 g of nylon 6 was packed into a glass column (20 mm i.d.×500 mm in length) by a wet packing method. The column volume of the column of polyamide was about 80 mL. Thereafter, 1000 ml of an aqueous kukoamine solution having a concentration of about 400 μg/mL, i.e. a crude extract solution formulated as in Example 1, was added into the chromatography column, and flowed slowly at a rate of 1.50 to 2 mL/min. The effluent was discarded. When no more solution flowed, additional 400 mL distilled water was flowed at a rate of 4 to 6 mL/min, and the effluent was discarded. Then, 400 mL of 50 vol % ethanol solution was flowed at the same rate as above, and the effluent was discarded. Then, 400 mL 0.5 vol % aqueous acetic acid solution was flowed at a rate of 2 mL/min, and the eluate was collected. The collected eluate was dried in a freeze-drier, and was weighed to give 286 mg of the crude extract of kukoamine. As determined by HPLC (using the same method and instrument as in Example 1), the kukoamine had a purity of about 54%. As a result of calculation using the same formula and index as in Example 1, after the solid phase column extraction, the enrichment rate of kukoamines was 36, that is, the content after column treatment was as much as 36 times of that in the initial crude extract. The yield was 40%.

Figure 7A:
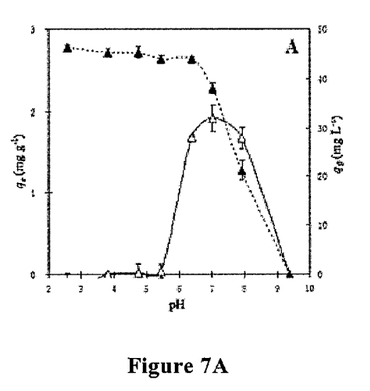
FIG. 7 shows influence of pH value on stability of kukoamine and of nylon 6 on its adsorption capacity. In the figure, solid triangles and hollow diamonds represent actual concentrations of kukoamines A and B after standing for 3 hours at different pH values, respectively. Hollow trangles and hollow diamonds represent adsorption capacity of kukoamines A and B adsorbed on nylon 6 at different pH values, respectively.
Figure 7B:
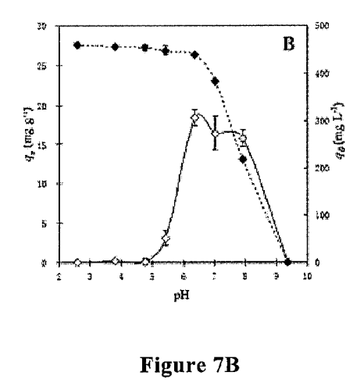
Figure 8A:
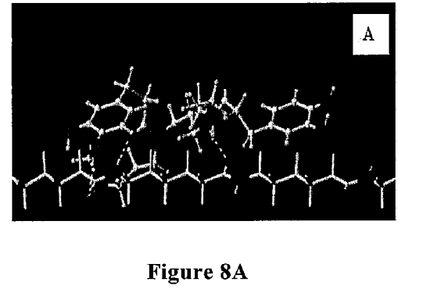
FIG. 8A and FIG. 8B show a computer-simulated interaction between kukoamine B (FIG. 8A), A (FIG. 8B) and nylon 6. In the figure, C is represented by white color, O is represented by red color, H is represented by green color, N is represented by blue color, and interactive hydrogen bond is represented by yellow color. As shown in the figure, the hydrogen bonds of kukoamine and nylon 6 occur between amino and carbonyl groups of guest and host molecules.
Figure 8B:
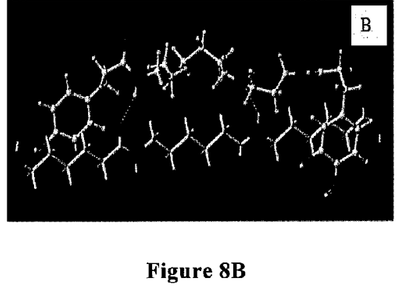

Mechanism of Adsorption of Kukoamine onto Polyamide:

As shown in FIG. 7, kukoamine is one kind of substances very sensitive to pH. Such substances are unstable, and are prone to degradation under an alkaline condition. Adsorption of kukoamine onto nylon 6 only occurs under neutral and weakly alkaline conditions. Such an adsorption is right in reverse to conventional adsorption of polyphenols onto nylon 6. The latter is adsorbed under an acidic condition, and is desorbed or eluted in the presence of organic alcoholic solution. The adsorption described in the present application, however, occurs under neutral and weakly alkaline conditions, and desorption only occurs under acidic conditions. Therefore, it can be seen that the adsorption site of kukoamines onto nylon is totally different from the adsorption site of polyphenols onto nylon, i.e., the adsorption is not possibly caused by hydrogen bonds formed between phenol hydroxyls and nylon 6. Therefore, in view of molecular structure of the compound, in the present invention, the adsorption most likely occurs because of the inter-attraction between amino groups and carbonyl groups of nylon 6. As a result, each of substances having similar structures as nylon 6 may adsorb kukoamines. The computer-simulated data further verified our opinions (see FIG. 8).

The disclosures above have described fundamentals, features and advantages of the present invention. An ordinary person skilled in this art would understand that the present invention is not limited by the above mentioned examples, which is intended to describe principles of the present invention together with description in the specification. Various changes and modifications may be made in the present invention without departing from principles and spirit of the invention, the scope of which is defined in the appended claims and their equivalents.

We claim:

1. A process for isolating kukoamine, comprising contacting a polyamide or a derivative thereof as an immobile phase with a solution of a crude extract of kukoamine.

2. A process according to claim 1, wherein the polyamide is polyamide 6, polyamide 66, polyamide 1010 or polyaramide.

3. A process according to claim 1, wherein the kukoamine is any one of compounds having the following structures or a mixture thereof:

Kukoamine derivative 3

Kukoamine derivative 4

Kukoamine derivative 5

Kukoamine derivative 6

Kukoamine derivative 7

4. A process according to claim 1, further comprising eluting the kukoamine from the immobile phase with an acidic solution after contacting.

5. A process according to claim 4, wherein the acidic solution has a pH of less than 5, and is an aqueous or alcoholic solution of acetic acid or a salt thereof, formic acid, hydrochloric acid, phosphoric acid or a salt thereof or trifluoroacetic acid.

6. A process according to claim 5, wherein the acidic solution is an aqueous solution of acetic acid having a concentration between about 0.1 vol % and 5 vol %.

7. A process according to claim 6, wherein the acidic solution is an aqueous solution of acetic acid having a concentration of about 0.5 vol %.

8. A process according to claim 1, further comprising dispersing the crude extract of kukamine in a polar solvent before contacting.

9. A process according to claim 8, wherein the polar solvent is water, or an aqueous solution of alcohol, acetonitrile or acetone having a concentration of about 10 vol % to 50 vol %.

10. A process according to claim 4, further comprising washing the immobile phase with water and an aqueous solution of alcohol respectively, after contacting and before eluting.

11. A process according to claim 4, further comprising washing the immobile phase with water and a aqueous solution of methanol or ethanol of about 50 vol % respectively, after contacting and before eluting.

12. A process according to claim 4, further comprising purifying the isolated kukoamine after eluting.

13. A process according to claim 12, wherein the purification is carried out by using a preparative or semi-preparative liquid chromatography.

14. A process according to claim 12, wherein the purification is carried out by using low pressure, middle pressure or high pressure liquid chromatography.

* * * * *